(12) United States Patent
Beaupré

(10) Patent No.: US 10,052,794 B2
(45) Date of Patent: Aug. 21, 2018

(54) METHODS AND SYSTEMS USING CONCRETE MIX TEMPERATURE MEASUREMENT

(71) Applicant: I.B.B. RHÉOLOGIE INC., Quebec (CA)

(72) Inventor: Denis Beaupré, Sainte-Catherine-de-la-Jacques-Cartier (CA)

(73) Assignee: COMMAND ALKON DUTCH TECH B.V., Birmingham, AL (US)

( * ) Notice: Subject to any disclaimer, the term of this patent is extended or adjusted under 35 U.S.C. 154(b) by 454 days.

(21) Appl. No.: 14/441,412

(22) PCT Filed: Nov. 8, 2013

(86) PCT No.: PCT/CA2013/050857
§ 371 (c)(1),
(2) Date: May 7, 2015

(87) PCT Pub. No.: WO2014/071526
PCT Pub. Date: May 15, 2014

(65) Prior Publication Data
US 2015/0298351 A1    Oct. 22, 2015

Related U.S. Application Data

(60) Provisional application No. 61/724,301, filed on Nov. 9, 2012.

(51) Int. Cl.
*B28C 5/42*    (2006.01)
*B01F 15/02*    (2006.01)
(Continued)

(52) U.S. Cl.
CPC .......... *B28C 5/4231* (2013.01); *B01F 3/1214* (2013.01); *B01F 13/0037* (2013.01);
(Continued)

(58) Field of Classification Search
CPC ....... B28C 5/422; B28C 5/4231; B28C 7/022; G01N 33/383
(Continued)

(56) References Cited

U.S. PATENT DOCUMENTS 4,915,297 A * 4/1990 Norman .................. B28C 7/003
                                                                  122/20 A
5,695,280 A * 12/1997 Baker .................... B28C 7/0007
                                                                  366/17
(Continued)

FOREIGN PATENT DOCUMENTS

EP      0303554 A2    2/1989
GB      2111399 A     7/1983
(Continued)

*Primary Examiner* — Tony G Soohoo
*Assistant Examiner* — Elizabeth Insler
(74) *Attorney, Agent, or Firm* — Norton Rose Fulbright Canada LLP; Alexandre Daoust

(57) ABSTRACT

The temperature of concrete can be monitored by a temperature probe. Typically, large volumes of concrete such as are typically carried in mixer trucks or mixed in industrial concrete production drums have a relatively stable, or slowly varying temperature, given the high thermal capacity of concrete. A sudden change in temperature can thus be attributed to an external event. A sudden addition of even a relatively small amount of water for instance, which has an even higher thermal capacity, can produce a notable sudden change in temperature. Examples where the detection of the addition of water can be particularly useful in the production and/or transport of concrete are provided herein. Moreover, if the temperature of the added water is known, and the quantity of concrete is also known, the sudden difference in temperature can be correlated to a volume of added water.

10 Claims, 1 Drawing Sheet

(51) Int. Cl.
  *B01F 3/12* (2006.01)
  *B01F 15/00* (2006.01)
  *B01F 13/00* (2006.01)
  *B28C 7/02* (2006.01)
  *B28C 7/04* (2006.01)
  *B28C 7/12* (2006.01)
  *G01N 33/38* (2006.01)

(52) U.S. Cl.
  CPC .. *B01F 15/00155* (2013.01); *B01F 15/00175* (2013.01); *B01F 15/0216* (2013.01); *B28C 5/422* (2013.01); *B28C 7/02* (2013.01); *B28C 7/0418* (2013.01); *B28C 7/12* (2013.01); *G01N 33/383* (2013.01); *B01F 2215/0047* (2013.01)

(58) Field of Classification Search
  USPC .............................................. 366/7
  See application file for complete search history.

(56) References Cited

U.S. PATENT DOCUMENTS

2007/0023551 A1    2/2007  Aichinger et al.
2011/0004332 A1*   1/2011  Andersen ............ C04B 40/0032
                                                700/103

FOREIGN PATENT DOCUMENTS

| JP | 2003193680 A | 7/2003 |
| WO | 02064262 A2 | 8/2002 |
| WO | 2011042880 A1 | 4/2011 |

* cited by examiner

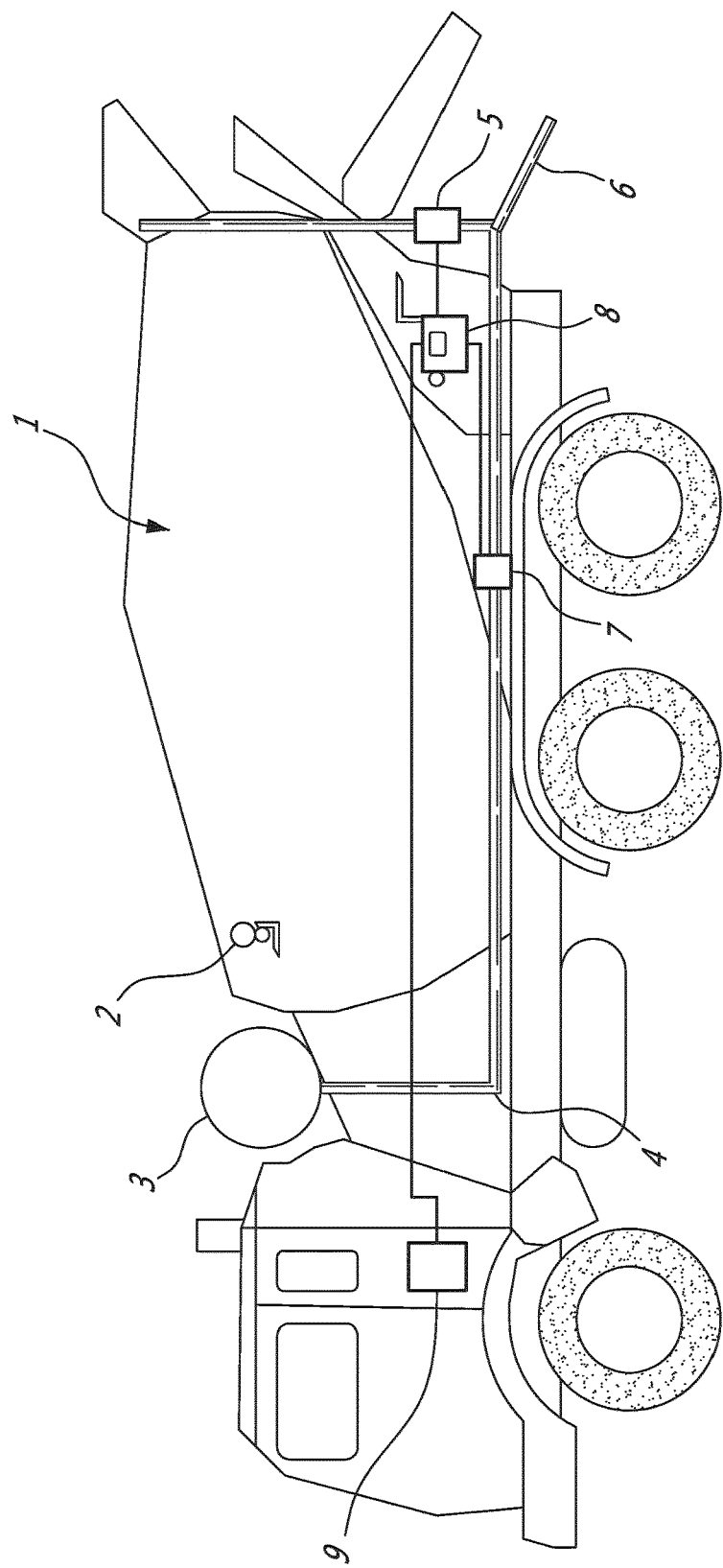

METHODS AND SYSTEMS USING CONCRETE MIX TEMPERATURE MEASUREMENT

BACKGROUND

Although using temperature probes to measure the temperature of concrete in industrial mixers has been widespread, the use of temperature probes in mixer trucks has significantly increased in recent years. This has opened the door to new opportunities in terms of potential uses of temperature measurement.

SUMMARY

In accordance with one aspect, there is provided a method of using temperature measurements of concrete in a mixer drum, the method comprising: obtaining a sudden temperature variation threshold of said concrete for said period of time; determining an actual temperature variation of said concrete over said given period of time using said temperature measurements; comparing the actual temperature variation to the sudden temperature variation threshold; and generating a signal based on said comparison.

In accordance with another aspect, there is provided a method of using temperature measurements of concrete in a mixer drum, the method comprising: adding water to the concrete in the mixer drum; obtaining a quantity and a thermal capacity of the concrete in the mixer drum prior to said adding; obtaining a temperature of said water added to the mixer drum; calculating the amount of water added to the mixer drum based on said quantity and thermal capacity of the concrete and said temperature of said water.

In accordance with another aspect, there is provided a method of using temperature measurements of concrete in a mixer drum, said method comprising: determining a temperature evolution curve projection for said concrete over a period of time; comparing the measured temperature of the concrete to said temperature evolution curve to associate the concrete to a moment in time of said period of time; and generating a signal based on said comparison.

In accordance with another aspect, there is provided a method of using temperature measurements of concrete in a mixer drum, said method comprising: obtaining a target temperature of the concrete; determining a temperature of water in a water system; obtaining a quantity and a thermal capacity of said concrete in the mixer drum; calculating an amount of said water to be added to the mixer drum to reach said target temperature based on said quantity and thermal capacity of the concrete and said measured temperature of said water; and adding the calculated amount of water from the water system to the mixer drum.

Many further features and combinations thereof concerning the present improvements will appear to those skilled in the art following a reading of the instant disclosure.

DESCRIPTION OF THE FIGURES

In the figures,

FIG. 1 is an example mixer truck.

DETAILED DESCRIPTION

The temperature of concrete can be monitored by a temperature probe. Typically, large volumes of concrete such as are typically carried in mixer trucks or mixed in industrial concrete production drums have a relatively stable, or slowly varying temperature, given the high thermal capacity of concrete (which, depending of specific formulations, can be around 2700 kJ/m$^3$/° C. for instance). A sudden change in temperature can thus be attributed to an external event. A sudden addition of even a relatively small amount of water for instance, which has an even higher thermal capacity, can produce a notable sudden change in temperature.

Examples where the detection of the addition of water can be particularly useful in the production and/or transport of concrete are provided below.

Moreover, if the temperature of the added water is known, and the quantity of concrete is also known, the sudden difference in temperature can be correlated to a volume of added water. This also can be useful, as will be exemplified below.

After mixing the components thereof, concrete temperature may start to rise due to internal heat generation cause by slow hydration. This temperature variation can be projected as a function of external temperature and/or water addition. Henceforth, measuring the temperature of concrete can allow determining when the concrete mixing has reached a given stage of evolution and can be used, for instance, in determining when to stop mixing the concrete. Further, the actual temperature can be monitored, and compared to the temperature projection, in which case detecting a temperature which suddenly departs from the temperature projection can be attributed to an external influence such as the addition of water.

Let us now turn to a specific example of a ready-mix truck as shown in FIG. 1 to provide examples where such uses of concrete temperature measurements can be beneficial. In this example, the ready-mix truck is equipped with a drum (1) that can be used to deliver fresh concrete. The drum is equipped with an internal wireless volume and temperature sensor (2) that sends data to a processing unit (8). The ready-mix truck further has a water system which includes a water tank (3); a water pipe (4) intended to be used in providing water inside the drum, the water pipe (4) being equipped with an optional water meter (5) (e.g. a flow meter); and a washing hose (6). In this embodiment, the washing hose reaches the opening of the water tank (3) and can thus also be used to add water into the concrete and bypasses the water meter in a manner that any water added into the concrete by the washing hose (6) rather than the water pipe (4) goes unmonitored by the water meter, if any. Further, the water system in this embodiment includes a water temperature sensor (7) that is connected to the processing unit (8). The processing unit (8) can be link to a communication system (9) to send alarm and data to a remote location, for instance, and can alternately be incorporated in a personal communications device.

Water-cement ratio (W/C) of a concrete mix, i.e. the ratio of weight of water to the weight of cement, is an important parameter in obtaining satisfactory properties in the concrete produced, such as satisfactory workability, strength and durability. W/C is normally controlled at the batching plant where the amount of water and cement are controlled during initial manufacturing of fresh concrete. However, the W/C can become altered thereafter, such when water is later added to increase the workability of the concrete, for instance, which can negatively affect the strength and durability of the concrete produced.

Adding water to concrete in the truck either by fixed pipe or the washing hose affects the W/C. In some cases, people can be motivated to add water to the concrete to improve workability but do not want this to be known because of the potential negative effects. In the example provided above, either one of 1) the addition of external water at a check point without using the water pipe; 2) the use of the washing hose by the driver to add water rather than the water pipe; or 3) the use of an alternative water supply at the delivery site would all go undetected by the flow meter of the water pipe, biasing the measurement of added water to a minimum value rather than a total effective amount.

Using the example mixer truck described above, the temperature of the concrete in the mixer truck can be measured in real time using the temperature sensor (2). The processor unit (8) can monitor the temperature, and especially in cases where the temperature of the added water is significantly different from the temperature of the concrete, it can have a program to detect the sudden increase in temperature which would be caused by unauthorized addition of water from any one of the three potential sources identified above.

The temperature of the added water, and the amount of concrete left in the drum at the time water is added is an important parameter to determine a current value of W/C. The temperature of the water from the water tank can be obtained by way of a temperature sensor (7). Positioning the flow meter (5) upstream from both the water pipe (3) and the washing hose (4) can allow obtaining a positive confirmation as to whether or not the added water comes from the water tank or not and whether this temperature measurement can be used, if this is considered relevant in a given application. On the other hand, there are many ways to obtain indications of the amount of concrete in the drum. For instance, the initial amount of concrete can be known or obtained. It can also be known that the delivery of the concrete has not yet begun and so the initial amount is still in the drum. One method to obtain an estimation of the amount of concrete is to count the number of rotations in the delivery direction (as oppose to ready-mix drum mixing direction) to estimate the amount of concrete left in the drum. However, because concrete is not always discharged in a continuous way and that the amount of concrete discharged in one drum turn depends on the concrete workability, this form of volume determination can underestimate the amount of concrete left in the drum of the ready-mix. Alternative methods include: 1) Load cell estimation the weight of concrete in the drum (weight and volume can easily be converted using the concrete density); 2) Using a pressure sensor inside the drum and measuring the time the sensor spends in the fresh concrete in one turn at constant speed; 3) Using a pressure sensor inside the drum and measuring the total angle the sensor has traveled inside the fresh concrete in one turn; 4) Using a moisture sensor on the surface of the drum measuring the angle the sensor traveled along the fresh concrete in one turn. All these latter measuring methods use some sort of calibration function, chart or table.

Using any one of these methods to measure the amount of concrete in the drum, and knowing the temperature of the added water, one can determine the amount of water added upon an occurrence of temperature variation within a level of uncertainty which can depend on the uncertainty of the other variables, and particularly the degree of variation in temperature.

Further, obtaining an indication of the amount of added water and an indication of the amount of concrete which remained in the drum at each water addition occurrence, is a first step in calculating, or actualizing, the new W/C; assuming that the initial composition of concrete is also known.

Example

In the northern hemisphere, (Canada, USA, Europe etc) it is common, to have concrete temperature specified to be above 20 C while the water temperature in the water tank of the ready-mix tank can be around 10 C. Adding only 7 kg of water at 10 C into 1 m3 of concrete at 20 C will create sudden change of temperature of more than 0.1 C which is easy to detect with a proper temperature sensor installed in the drum of the ready-mix.

It will be noted that the description provided above is intended to be exemplary only. For instance, further to the detection of a sudden change in temperature, the system can be further enhanced by the definition and use of an alarm that will warn relevant (such as quality control or production) personnel. This alarm can be further broadcast by a proper communication system (radio signal, cellular technology, wi-fi of the like) to more people and location as part of a global system. Further to the detection of a sudden change in temperature, the use of a temperature sensor can be installed into the water tank or into the pipe line between the water tank and the drum of the ready-mix truck (7). By combining the sudden change in concrete temperature with the actual temperature of the added water as determine with the water temperature sensor. It is possible to calculate the change in W/C provided the discharged of concrete has not started. Further to the calculation of the W/C for a complete load of concrete, an alarm can be used to warn relevant (such as quality control or production) personnel if the W/C has been changed (usually to higher values) up to define limits. This alarm can be further broadcast by a proper communication system (radio signal, cellular technology, wi-fi of the like) to more people and location as part of a global system. The calculation of change in W/C can be obtained for all quantity (complete and partial load) of concrete into the drum by combining the data from three sensors: the concrete temperature sensor (2), the water temperature sensor (7), and the sensor that allow to establishing in real time the volume of concert into the drum of the ready mix (2). When the dada from all the three sensors are combined, it is possible to calculate the amount of water added using the thermal capacity of concrete (calculated based on composition) and the W/C of the full or partial concrete load. Further to the calculation of the W/C for a partial load of concrete, an alarm can be used to warn relevant (such as quality control or production) personnel if the W/C has been changed (usually to higher values) up to define limits. This alarm can be further broadcast by a proper communication system (radio signal, cellular technology, wi-fi of the like) to more people and location as part of a global system.

As can be understood, the examples described above and illustrated are intended to be exemplary only. The scope is indicated by the appended claims.

What is claimed is:

1. A method of using a temperature measurement of water in association with a concrete mixer drum, the method comprising:
   adding water to the concrete in the mixer drum;
   measuring an actual temperature variation of said concrete due to said water addition;
   obtaining a quantity and a thermal capacity of the concrete in the mixer drum prior to said adding water;
   obtaining a temperature of said water added to the mixer drum;
   using a processor unit, calculating the amount of water added to the mixer drum based on said quantity, said actual temperature variation and thermal capacity of the concrete and said temperature of said water;

wherein said obtaining a quantity of the concrete in the mixer drum includes measuring the quantity of concrete in the mixer drum.

2. The method of claim 1 wherein said obtaining a temperature of said water added to the mixer drum includes measuring the temperature of water in a water tank.

3. The method of claim 2 further comprising determining that said added water comes from the water tank.

4. The method of claim 1 further comprising obtaining a water-cement ratio of said concrete prior to said adding water, and updating said water-cement ratio based on the calculated amount of water and the obtained quantity of concrete in the mixer drum.

5. A method of using a temperature measurement of water in association with a concrete mixer drum, the method comprising:

adding water to the concrete in the mixer drum;

measuring an actual temperature variation of said concrete due to said water addition;

obtaining a quantity and a thermal capacity of the concrete in the mixer drum prior to said adding water;

obtaining a temperature of said water added to the mixer drum;

using a processor unit, calculating the amount of water added to the mixer drum based on said quantity, said actual temperature variation and thermal capacity of the concrete and said temperature of said water;

further comprising obtaining a water-cement ratio of said concrete prior to said adding water, and updating said water-cement ratio based on the calculated amount of water and the obtained quantity of concrete in the mixer drum.

6. The method of claim 5 wherein said obtaining a quantity of the concrete in the mixer drum includes measuring the quantity of concrete in the mixer drum.

7. The method of claim 5 wherein said obtaining a temperature of said water added to the mixer drum includes measuring the temperature of water in a water tank.

8. The method of claim 7 further comprising determining that said added water comes from the water tank.

9. A method of using temperature measurements of concrete in a mixer drum, the method comprising:

adding water to the concrete in the mixer drum;

obtaining a quantity and a thermal capacity of the concrete in the mixer drum prior to said adding water;

obtaining a temperature of said water added to the mixer drum;

using a processor unit, calculating the amount of water added to the mixer drum based on said quantity and thermal capacity of the concrete and said temperature of said water.

10. The method of claim 9 further comprising comparing said calculated amount of water to an authorized amount of water, and generating an alert indicating an unauthorized addition of water when the calculated amount of water exceeds the authorized amount of water by a given tolerance.

* * * * *